United States Patent
Sarwar et al.

(10) Patent No.: US 9,383,375 B2
(45) Date of Patent: Jul. 5, 2016

(54) AUTOMATIC ANALYSIS DEVICE (71) Applicant: HITACHI HIGH-TECHNOLOGIES CORPORATION, Tokyo (JP)

(72) Inventors: Sayaka Sarwar, Tokyo (JP); Hiroki Mori, Tokyo (JP); Miki Taki, Tokyo (JP); Yoichi Aruga, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/366,095

(22) PCT Filed: Dec. 12, 2012

(86) PCT No.: PCT/JP2012/082162
§ 371 (c)(1),
(2) Date: Jun. 17, 2014

(87) PCT Pub. No.: WO2013/094485
PCT Pub. Date: Jun. 27, 2013

(65) Prior Publication Data
US 2014/0322080 A1     Oct. 30, 2014

(30) Foreign Application Priority Data

Dec. 22, 2011  (JP) .................................. 2011-281882

(51) Int. Cl.
| | |
|---|---|
| G01N 35/00 | (2006.01) |
| G06F 3/048 | (2013.01) |
| G06F 3/0482 | (2013.01) |
| B01L 3/00 | (2006.01) |

(52) U.S. Cl.
CPC .......... *G01N 35/00663* (2013.01); *B01L 3/527* (2013.01); *G01N 2035/0091* (2013.01); *G01N 2035/00673* (2013.01); *G01N 2035/00891* (2013.01)

(58) Field of Classification Search
CPC ............... G01N 35/00663; G01N 2035/00673
See application file for complete search history.

(56) References Cited

U.S. PATENT DOCUMENTS 7,698,654 B2 *  4/2010  Fong ..................... G06F 3/0482
                                                        715/810
2008/0165125 A1    7/2008  Hosono
(Continued)

FOREIGN PATENT DOCUMENTS

| JP | 10-096733 A | 4/1998 |
|---|---|---|
| JP | 3314629 B2 | 6/2002 |

(Continued)

OTHER PUBLICATIONS

International Preliminary Report on Patentability received in International Application No. PCT/JP2012/082162 dated Jul. 3, 2014.
(Continued)

*Primary Examiner* — P. Kathryn Wright
(74) *Attorney, Agent, or Firm* — Mattingly & Malur, PC (57) ABSTRACT

An automatic analysis device may enable easy selection of a desired reagent-setting position and efficient execution of reagent information confirmation and reagent usage setup by displaying, at a high level of visibility and in an enlarged format, both of the selected reagent-setting position and means for moving, for example, a mouse pointer to an anterior or posterior display position with respect to the selected reagent-setting position. A display controller may cause display of a list of reagent-setting positions provided in a reagent disk. An extended display controller may cause display, in an enlarged format, of a reagent-setting position that has been selected from the reagent-setting position list displayed by the display controller. The display of the selected reagent-setting position may be enlarged distinctly from that of other reagent-setting positions. A movement controller may select a reagent-setting position displayed next to the reagent-setting position being displayed in the enlarged format.

10 Claims, 5 Drawing Sheets

(56) References Cited

U.S. PATENT DOCUMENTS

| | | |
|---|---|---|
| 2009/0074616 A1 | 3/2009 | Sento et al. |
| 2010/0114501 A1 | 5/2010 | Kondou et al. |
| 2011/0138275 A1* | 6/2011 | Yu .................................. 715/702 |
| 2013/0009988 A1 | 1/2013 | Tokunaga et al. |

FOREIGN PATENT DOCUMENTS

| | | |
|---|---|---|
| JP | 2007-333466 A | 12/2007 |
| JP | 2007333466 A * | 12/2007 |
| JP | 2009-074874 A | 4/2009 |
| JP | 2010-107433 A | 5/2010 |
| JP | 2010-256051 A | 11/2010 |
| JP | 4659767 B2 | 1/2011 |
| JP | 2011-203115 A | 10/2011 |
| WO | 2011/037069 A1 | 3/2011 |

OTHER PUBLICATIONS

Extended European Search Report received in corresponding European Application No. 12860678.7 dated Jul. 17, 2015.

* cited by examiner

AUTOMATIC ANALYSIS DEVICE

TECHNICAL FIELD

The present invention relates generally to automatic analysis devices that analyze blood, urine, and other samples, and more particularly, to an automatic analysis device suitable for displaying information about reagents.

BACKGROUND ART

Automatic analysis devices analyze blood, urine, and other samples. Such device's manufacturers have been making various efforts to simplify the work associated with these devices. Much of the work is occupied by the calibration, maintenance, reagent changes, and other jobs that a user performs before and after measuring patient samples. The reagent changes, in particular, are among the jobs that the user absolutely needs to perform on a daily basis. If the reagents needed for the day's measurement are not set in the device beforehand, a lack of the reagents during the measurement of the patient samples is likely to cause no measurement result output, thus leading to a delay in reporting the results to the patients. In addition, expiration dates of the reagents used in automatic analysis devices are predetermined and use of an expired reagent is likely to cause output of inaccurate measurement results. For these reasons, the user also confirms whether the reagents that have been set in the device are within the expiration dates.

On a reagent management screen displayed by a conventional general-purpose automatic analysis device, various information, including analytical name of items, residual quantities, manufacturing lot numbers, serial numbers, and expiration dates, is displayed for each of reagent positions within a reagent disk. The reagents that need to be changed may be displayed at an upper section of a list as an example of various measures and ways to alert the user.

In addition to the screen displayed by the automatic analysis device, in order to allow the user to readily recognize a position in which to set a new reagent when he or she is to actually change reagents, independent indicator elements or display elements may be disposed inside the reagent disk for each of setting positions for the reagents to be changed (Patent Document 1, for example, discloses such a technique). In addition, status information on calibration, quality control, and reagents may be collectively displayed to allow the user to readily identify a problematic reagent (Patent Document 2, for example, discloses such a technique).

PRIOR ART LITERATURE

Patent Documents

Patent Document 1: Japanese Patent No. 3314629
Patent Document 2: Japanese Patent No. 4659767

SUMMARY OF THE INVENTION

Problems to be Solved by the Invention

With the functional diversification of automatic analysis devices to accommodate the increase in the number of analyzable items in recent years, the number of kinds of reagents mountable in an automatic analysis device is also increasing and the amount of reagent information displayed on a screen is correspondingly increasing. Additionally, an increase in throughput is making it necessary to change and add reagents more frequently than before. At the same time, however, a need to use a wider range of screens for executing these jobs is increasing the amount of time and effort required for screen switching by click operations. In this context, it is being desired that existing automatic analysis devices be improved in the ease of operations.

The technique described in Patent Document 1 is expected to reduce human errors in reagent changes. This conventional technique, however, provides an independent reagent-screen display in addition to the screen display by the automatic analysis device. This implies that significant changes in both hardware and software would be unavoidable.

The technique described in Patent Document 2 is estimated to enable easy identification of a problematic reagent. Solving the problem, however, would require shifting the screen to a reagent management screen, and in such cases as that a plurality of problematic reagents exist, frequent screen shifts may be needed, which if actually so, will require a great deal of time and effort.

An object of the present invention is to provide an automatic analysis device that enables easy selection of a desired reagent-setting position and efficient execution of reagent information confirmation and reagent usage setup, by displaying, at a high level of visibility and in an enlarged format, both of the selected reagent-setting position and means for moving, for example, a mouse pointer to an anterior or posterior display position with respect to the selected reagent-setting position.

Means for Solving the Problems (1) In order to attain the above object, an aspect of the present invention is an automatic analysis device for analyzing a sample automatically and determining concentrations of components contained in the sample, the device including a reagent container mounting mechanism for mounting a plurality of reagent containers needed for measurement, and a display controller for displaying a list of reagent-setting positions in the reagent container mounting mechanism. The display controller has an extended display controller that displays, in an enlarged format, a reagent-setting position that has been selected from the reagent-setting position list displayed by the display controller, the display of the selected reagent-setting position being enlarged distinctly from that of other reagent-setting positions, and a movement controller that selects a reagent-setting position displayed next to the reagent-setting position being displayed in the enlarged format.

With the above device configuration, both of the selected reagent-setting position and means for moving, for example, a mouse pointer to a display position anterior or posterior to that reagent-setting position can be displayed at a high level of visibility and in the enlarged format. This display enables easy selection of the desired reagent-setting position and efficient execution of reagent information confirmation and reagent usage setup.

(2) The movement controller in above item (1) is preferably configured to display a scroll button at both sides of a section displayed in the enlarged format in the reagent-setting position list by the extended display controller, and to display the scroll buttons themselves in an enlarged format by enlarging the display of the reagent-setting positions in the reagent-setting position list.

(3) The display controller in item (1) is preferably configured to display, on one operating screen, the reagent-setting position list and a list of usage status information about reagents mounted in a container-accommodated condition in the reagent container mounting mechanism.

(4) The automatic analysis device in above item (3) is preferably configured to further include a synchronous display controller that displays, in a state operatively associated with the reagent usage status information during the display of the reagent-setting position list, usage status information about a reagent corresponding to the reagent-setting position selected via the selection means.

(5) The automatic analysis device in above item (3) is preferably configured to further include a synchronous display controller that displays, in operatively associated form in the reagent-setting position list, the reagent-setting position about a reagent corresponding to the reagent of usage status information selected via the selection means.

(6) In order to attain the above object, an aspect of the present invention is an automatic analysis device for analyzing a sample automatically and determining concentrations of components contained in the sample, the device including a reagent container mounting mechanism for mounting a plurality of reagent containers needed for measurement, and a display controller for displaying a list of reagent-setting positions provided in the reagent container mounting mechanism. The display controller has an extended display controller that displays, in an enlarged format, at least one reagent-setting position that has been selected via the selection means from the reagent-setting position list displayed by the display controller, the display of the selected reagent-setting position being enlarged distinctly from that of other reagent-setting positions, the extended display controller further making an enlarged display of, in addition to the selected reagent-setting position, other reagent-setting positions associated with the selected reagent-setting position.

With the above device configuration, both of the selected reagent-setting position and means for moving, for example, a mouse pointer to a display position anterior or posterior to that reagent-setting position can be displayed at a high level of visibility and in the enlarged format. This display enables easy selection of the desired reagent-setting position and efficient execution of reagent information confirmation and reagent usage setup.

Effects of the Invention

In either aspect of the present invention, easy selection of a desired reagent-setting position and efficient execution of reagent information confirmation and reagent usage setup can be achieved by displaying, at a high level of visibility and in the enlarged format, both of the selected reagent-setting position and the means for moving, for example, the mouse pointer to the display position anterior or posterior to the selected reagent-setting position.

MODE FOR CARRYING OUT THE INVENTION

Hereunder, a configuration and operation of an automatic analysis device according to an embodiment of the present invention will be described using FIGS. 1 to 5.

An overall configuration of the automatic analysis device according to the embodiment of the present invention is first described below using FIG. 1.

Figure 1:
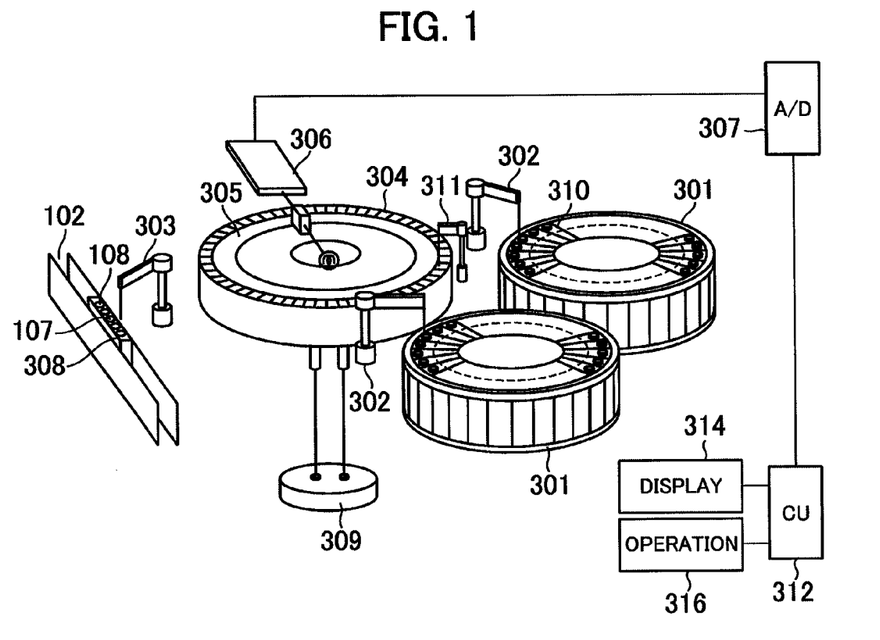
FIG. 1 is a plan view showing an overall configuration of an automatic analysis device according to an embodiment of the present invention.

FIG. 1 is a plan view showing the overall configuration of the automatic analysis device according to the embodiment of the present invention.

As shown in FIG. 1, the automatic analysis device of the present embodiment includes: a reagent section with a reagent disk 301, which is a reagent container accommodation unit, and with a reagent pipettor 302; a sampling section with a sample pipettor 303; a reaction section with a reaction disk 305 having reaction vessels 304; a measuring section with a multi-wavelength photometer 306 and an analog/digital converter 307; and a control section with a control unit 312, a display unit 314, and an operating unit 316.

A rack 107 with internally placed sample containers 108 is carried to a sample suction position 308 along a carriage unit 102. The sample pipettor 303 suctions a sample within the sample container 108 and then dispenses a predetermined amount of the sample into a reaction vessel 304.

The reaction vessel 304 with the sample solution dispensed thereinto is moved to a first reagent-adding position inside the reaction disk 305 communicating to a constant-temperature oven 309. At this time, the reagent disk 301 rotates so that a reagent container 310 corresponding to a current analytical item moves to a position under the reagent pipettor 302 held by elevating arm. The reagent pipettor 302 then suctions a predetermined amount of a first reagent and adds the first reagent to the reaction vessel 304 that has been moved to the first reagent-adding position. The reaction vessel 304 with the first reagent thus added thereto is moved to a stirrer 311, where first stirring takes place.

A beam of light that has been emitted from a light source passes through the reaction vessel 304 whose internal contents have been stirred, and then the beam enters the multi-wavelength photometer 306. The multi-wavelength photometer 306 then detects absorbance of a reaction solution, the internal contents of the reaction vessel 304. A signal that has resulted from the detection of the absorbance is sent to the analog/digital (A/D) converter 307 and then supplied to the control unit 312 via an interface. The control unit 312 converts the absorbance signal into a concentration of the analytical item corresponding to an internal substance of the sample solution that is to be measured.

After the measurement, the reaction vessel 304 is moved to a cleaning mechanism, then after having the internal solution discharged at a predetermined position for cleaning by the reaction vessel cleaning mechanism, cleaned with water, and reused for next analysis.

The control unit 312 also controls operation of the carriage unit 102, sample pipettor 303, reaction disk 305, reagent disk 301, reagent pipettor 302, and other mechanical elements.

The operating unit 316 is a mouse and/or a keyboard. The display unit 314, which provides a graphical user interface (GUI), displays an operating screen that allows an operator to perform predetermined operations by specifying them with the mouse and/or the like.

The operator can check a reagent state and more by manipulating the operating unit 316 while viewing details of the screen display on the display unit 314. Manipulation results of the operating unit 316 are controlled by the control unit 312 and incorporated into the details of the screen display on the display unit 314. When a touch panel is used as the display unit 314, the operating unit 316 is not necessary since the operator can operate the screen by merely touching the display screen of the display unit 314.

Next, a detailed configuration of the control section in the automatic analysis device according to the embodiment of the present invention is described below using FIG. 2.

Figure 2:
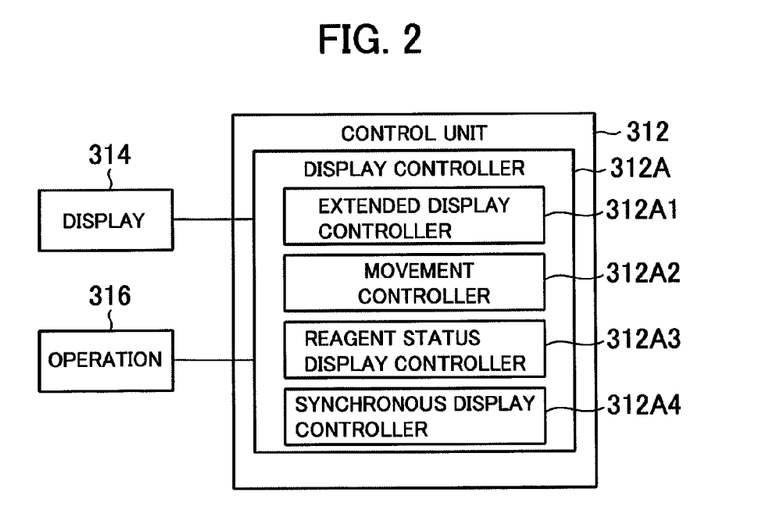
FIG. 2 is a block diagram showing a detailed configuration of a control section in the automatic analysis device according to the embodiment of the present invention.

FIG. 2 is a block diagram showing the detailed configuration of the control section in the automatic analysis device according to the embodiment.

The control section includes the control unit 312, the display unit 314, and the operating unit 316. The control unit 312 has a display controller 312A. The display controller 312A has an extended display controller 312A1, a movement controller 312A2, a reagent status display controller 312A3, and a synchronous display controller 312A4.

Operation of these elements of the display controller 312A will be described later herein using FIGS. 3A-3C onward.

Next, an example of an operating screen used in the automatic analysis device according to the embodiment of the present invention is described below using FIG. 3A.

Figure 3A:
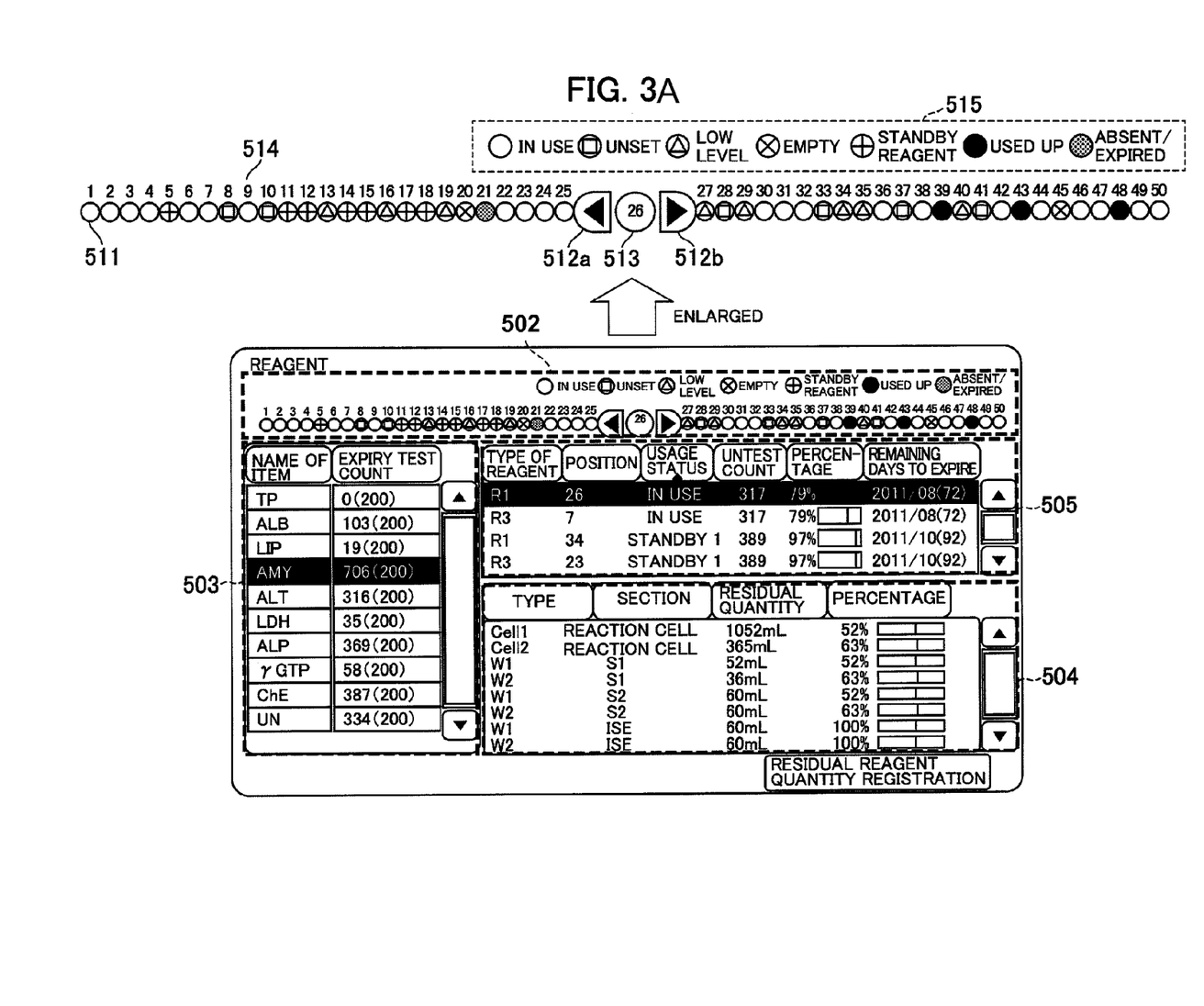
FIG. 3A-3C are explanatory diagrams of an operating screen, and portions thereof, used in the automatic analysis device according to the embodiment of the present invention.
Figure 3B:
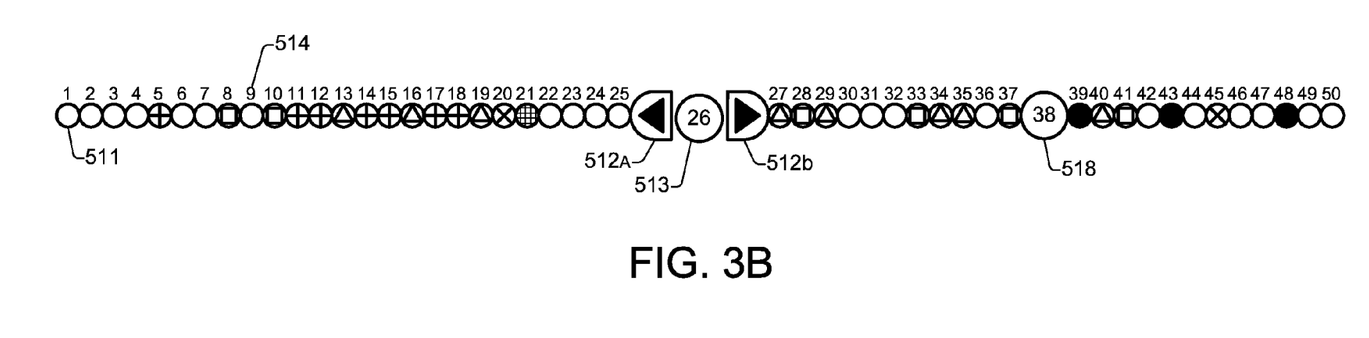
Figure 3C:
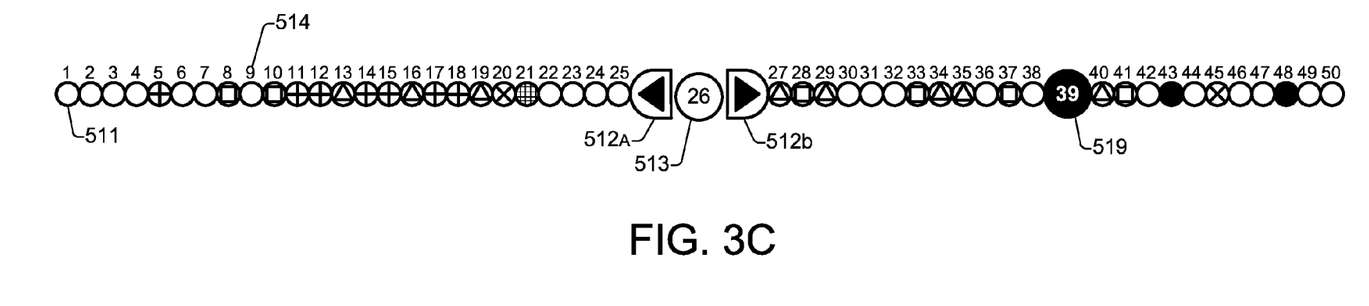

FIG. 3A is an explanatory diagram of the operating screen used in the automatic analysis device according to the embodiment.

The display screen refers to a system status/reagent management screen displayed by the display unit 314 of FIG. 2. The display controller 312A shown in FIG. 2 controls the display unit 314 to display the system status/reagent management screen shown in FIG. 3A.

The system status/reagent management screen is composed primarily of four regions, namely an operations guidance/reagent position listing region 502, an analytical item listing region 503, a detailed reagent display region 505, and a message list/system reagent display region 504. In general, the reagent management screen that an automatic analysis device displays is operated by a user for purposes such as requesting reagent registration, confirming whether a reagent that the user has set is properly recognized by and registered in the device, confirming a residual amount, expiration date, and manufacturing lot number of the reagent, and manually registering the reagent directly in an unregistered setting position. The reagent management screen, therefore, provides the information that the user needs to confirm on a daily basis such as before and after changing reagents.

The reagent position listing region 502 is where all reagent positions present on the reagent disk are displayed, and this listing region includes reagent position buttons 511 each corresponding to a specific reagent position, an extended display position button 513, scroll buttons 512a and 512b, and reagent position numbers 514. As many reagent position buttons 511 as there actually are reagent positions present on the reagent disk are displayed in the listing region 502. While the reagent positions are displayed horizontally in one row by way of example in FIG. 2, these reagent positions may be displayed in a pattern similar to that of an actual schematic pattern diagram. For example, they may be displayed in a disk shape matching a configuration of the reagent disk, in a limited, and yet, readily identifiable display range of an actual screen. The reagent position buttons 511 change respective display colors according to a particular state of a reagent status display color explanatory area 515 and based on information such as a current residual amount of reagent. Although the kinds of hatching are changed in FIG. 3A to represent differences in color between the buttons, the colors themselves are changed on a monitoring screen of an actual automatic analysis device. The reagent position listing region 502 is not displayed on a conventional display screen. All reagent positions can be readily understood by displaying the reagent position listing region 502.

For example, if reagent positions with a quantitative lack of a reagent are to be displayed in red, only these reagent positions of all the reagent-setting positions on the reagent disk that are listed in the reagent position listing region 502 may be displayed in red, so that the user can readily confirm currently unoccupied reagent positions and a total number thereof.

When the user selects any one of the reagent position buttons 511, the extended display controller 312A1 extends the display of the selected position to that of the extended display position button 513. Extending the display means enlarging the display of the selected position. The selected position and that of a plurality of reagent positions anterior and posterior to that position may both be displayed in an extended format. In this case, the currently selected reagent position can be identified more easily by extending the display of the same number of reagent positions in both anterior and posterior directions relative to that position, to a size slightly smaller than the extended display position button 513 and larger than the reagent position buttons 511. Additionally, since the anterior and posterior reagent positions are also displayed in the extended format, selectivity of these reagent positions can be enhanced by directly touching them on the screen.

Furthermore, the reagent position buttons 511 corresponding to the selected reagent position and other reagent positions associated with the selected reagent position are simultaneously displayed in extended form. For example, as illustrated in FIG. 3B, there is a case in which reagents of the same kind are accommodated in a plurality of reagent containers. In this case, suppose that for example, the 26th reagent and the 38th reagent are of the same kind. If the 26th reagent is selected in the reagent position listing region 502, the 26th reagent and the 38th reagent are displayed at the same time in extended form, as indicated at 513 and 518, respectively. In this manner, the reagent position buttons 511 corresponding to the selected reagent position and the position in which is set a reagent for the same analytical item as that of the selected reagent position are simultaneously displayed in extended form. In another case, as illustrated in FIG. 3C, two kinds of reagents (a first reagent and a second reagent) may be used for one analytical item. In this case, if the 26th reagent is the first reagent and the 39th reagent is the second reagent, since both are associated with one another, when the 26th reagent is selected in the reagent position listing region 502, the 26th reagent and the 39th reagent are displayed at the same time in extended form, as indicated at 513 and 519, respectively. In this manner, the reagent position buttons 511 corresponding to the selected reagent position and the position in which is set a reagent associated with the selected reagent position are simultaneously displayed in extended form.

The reagent position buttons 511 can be selected by directly touching these buttons if they are displayed on a touch panel, or by clicking mouse buttons. Additionally, when the scroll button 512a or 512b is pressed, the movement controller 312A2 moves, for example, a mouse pointer laterally to an anterior or posterior adjacent reagent position. In other words, although a current reagent position 26 is displayed in an extended state in the example of FIG. 3A, a press of the scroll button 512a under that state returns the display of the reagent position 26 to the same normal size as that of another reagent position button 511, while at the same time making an extended display of a reagent position 25 instead. Conversely, a press of the scroll button 512b during the extended display of the reagent position 26 returns the display of this reagent position to the same normal size as that of the reagent position button 511, while at the same time making an extended display of a reagent position 27 instead. The lateral movement of the mouse pointer by the scroll button 512a or 512b may be such that the pointer is moved in units of a plurality of positions and such that the plurality of positions are displayed in extended form. For example, if three positions are accommodated together in a container, moving the pointer through the three positions of space and displaying these positions in extended form allows the user to readily locate the positions.

At this time, the selectivity of these reagent positions can be enhanced by displaying the scroll buttons 512a and 512b in a size substantially equal to that of the extended display position button 513. In particular when a touch panel is used, displaying the scroll buttons 512 in the size substantially equal to that of the extended display position button 513 allows the user to select a desired reagent position button 511 more easily by touching with a finger. Existence of a larger number of positions on the reagent disk downscales the reagent position buttons more if displaying all positions in the limited screen range is attempted. Accordingly, it may become difficult to select a desired position accurately with one finger touch. When the scroll buttons 512 and the reagent position buttons 511 are displayed in large enough a size, however, even if the desired position cannot be selected with one touch, using the scroll buttons 512 or the extended display position button 513 allows the mouse pointer to be moved to the desired reagent position, for improved operability. If an attempt is made to display all reagent position buttons 511 in enlarged form, the buttons may number too many to fit into the screen of the limited display range, in which case, associated reagent information is not likely to be displayed. Making an extended display of the limited range, however, allows necessary information to be provided at a high level of visibility while maintaining the entire display of the reagent positions.

The analytical item listing region 503 is where are displayed the analytical items relating to components to be measured using the reagents set in or registered for the reagent disk, and expiry test counts corresponding to the analytical items. The analytical items displayed in the analytical item listing region 503 can have their order of display sorted according to name of item or expiry test count. For example, if an expiry test count is selected on the screen and the order of display is sorted, since the analytical items will be rearranged with one of the smallest expiry test count first, the user can easily confirm the analytical items for which the reagents set in the device are smaller in expiry test count.

The synchronous display controller 312A4 can operatively associate the analytical item listing region 503, the reagent position listing region 502, and the detailed reagent display region 505, with each other. Operatively associating these screen regions is another function that is not realized in conventional technology. The display of the screen regions in the operatively associated state enables selection of an item in one display region to be incorporated into another display region as well, thus enabling a status of related sections to be easily understood.

In the example of FIG. 3A, the reagent position that has been selected in the reagent position listing region 502 corresponds to a position number 26 denoting a position present on the reagent disk. At the moment the position 26 is selected, the position is displayed in extended form. Additionally, an analytical item for the reagent set in that position is displayed, for example, in color-coded form with an item name of AMY (short for amylase) to enable the user to readily discriminate AMY from other analytical items. The example of FIG. 3A indicates that the measurement relating to an analytical item of AMY can be repeated for 706 test cycles with the device-set reagent by confirming the corresponding expiry test count. While the reagent position number is displayed in the reagent position listing region 502, if the expiration date of the reagent is already exceeded, that position is displayed, for example, in color-coded form for distinction from unexpired-reagent positions. This allows the user to readily identify any expired-reagent positions.

The reagent status display controller 312A3 controls the device to display, in the detailed reagent display region 505, detailed information about a reagent bottle usage status relating to all corresponding analytical items, inclusive of the reagent position. The detailed information includes, for example, a remaining test count for the bottle, and a residual number of days for which the reagent can be used (remaining days to expire). During the display of the detailed information, the reagent bottle in the position currently being displayed in the extended format in the reagent position listing region 502 is displayed, for example, in color-coded form for distinction from other reagent bottles.

The same also applies in a case reverse to the above. That is to say, if an analytical item is selected in the analytical item listing region 503, the synchronous display controller 312A4 operatively associates the display of reagent information in the reagent position listing region 502 and the display of the detailed reagent information in the detailed reagent display region 505 automatically and displays the particular reagent in easily selectable and readily distinguishable form.

For example in the foregoing description, when the 26th reagent position in the reagent position listing region 502 is selected, those sections of the analytical item listing region 503 and detailed reagent display region 505 that relate to the 26th reagent position are displayed in a highlighted condition. When "AMY" is selected as an analytical item in the analytical item listing region 503, however, the 26th reagent position in the reagent position listing region 502 is displayed in the extended format and the details of the 26th reagent position in the detailed reagent display region 505 are displayed in a highlighted condition.

Similarly, when a reagent is selected in the detailed reagent display region 505, the synchronous display controller 312A4 operatively associates the display of the corresponding reagent information in the reagent position listing region 502 and the display of the reagent information in the analytical item listing region 503 automatically and displays the particular reagent in easily selectable and readily distinguishable form.

For example in the foregoing description, when the section of the detailed reagent display region 505 that relates to the 26th reagent position is selected, the 26th reagent position in the reagent position listing region 502 is displayed in the extended format and "AMY" is displayed in a highlighted condition as an analytical item in the analytical item listing region 503.

The system reagent display region 504 is where are displayed a usage status of system reagents set in a predetermined position other than the reagent disk. The system reagent includes a cleaning agent, for example. Information on fixed types of reagents (generally) set in outside positions of the reagent disk is displayed in the system reagent display region 504, so this display region does not always need to be operatively associated with the detailed reagent display region 505, the analytical item listing region 503, and the reagent position listing region 502. However, the analytical items may include one for which, depending on a combination of analytical items, cleaning with such a cleaning agent as used for avoiding a sample carry-over needs to precede or follow measurement before the measurement can be executed accurately. For this reason, automatic analysis devices are commonly designed so that cleaning with a cleaning agent can be specified for a particular combination of analytical items. In a case that a cleaning agent needed to measure a component corresponding to an analytical item is present, therefore, when the analytical item is selected in one of the detailed reagent display region 505, the analytical item listing region 503, and the reagent position listing region 502, in the system reagent display region 504, related system reagent information is displayed in operatively associated form distinctly from other system reagent information.

Next, details of the display control in the automatic analysis device according to the embodiment of the present invention are described below using FIG. 4.

Figure 4:
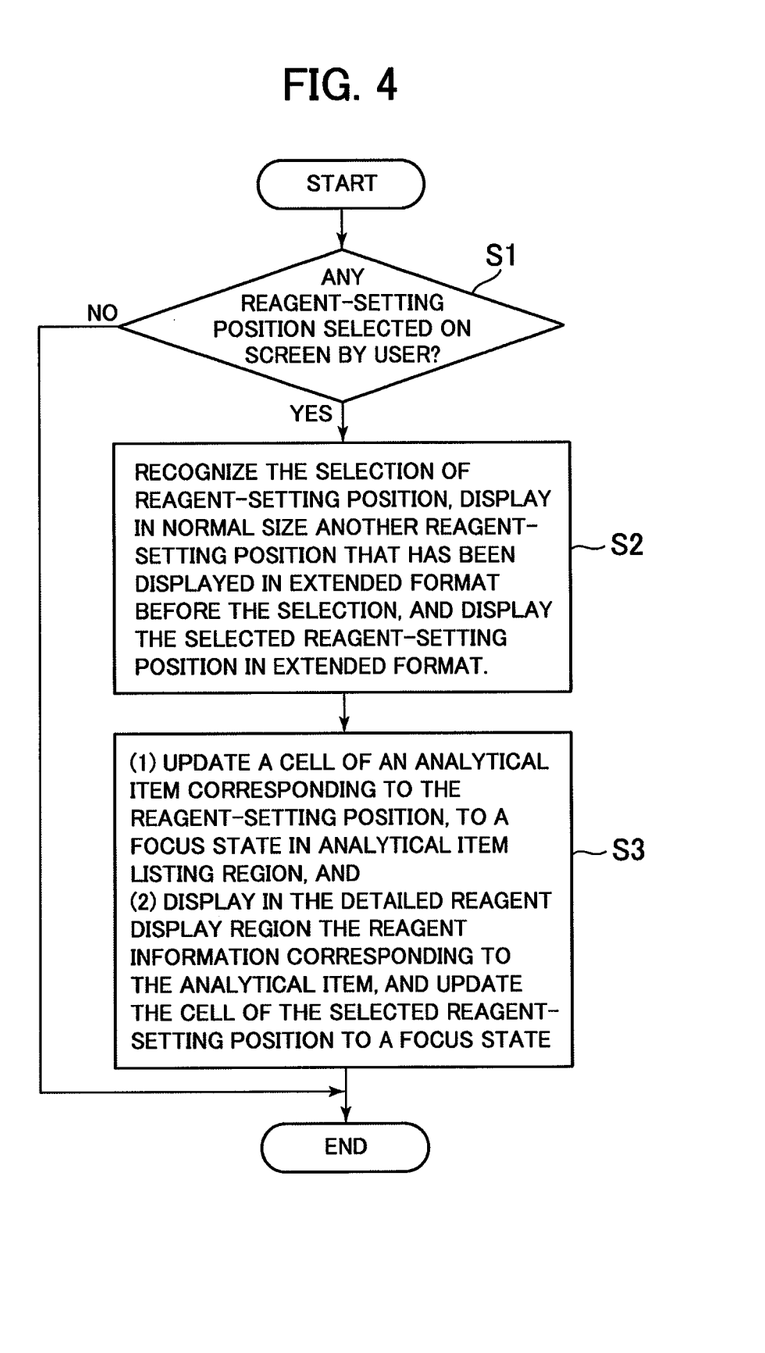
FIG. 4 is a flowchart that shows details of display control in the automatic analysis device according to the embodiment of the present invention.

FIG. 4 is a flowchart showing the details of the display control in the automatic analysis device according to the embodiment.

FIG. 4 shows logic designed to make an enlarged display of a reagent-setting position selected on the reagent management screen by the user, and then update corresponding cell display.

First, the user selects a desired reagent-setting position on the reagent management screen (step S1). Processing terminates if the selection is not conducted.

Upon recognizing the selection, the control section of the device displays in normal size another reagent-setting position that has been displayed in enlarged format before the selection, and then changes the display of the selected reagent-setting position to an enlarged display format (step S2).

Next, in step S3, the control section updates the cell display of the analytical item corresponding to the reagent-setting position, to a focus state in the analytical item listing region 503. The control section further makes a detailed reagent display of the reagent information corresponding to the analytical item. At the same time, the control section updates to a focus state the cell display of the reagent information corresponding to the reagent-setting position that was selected in step S2.

At this time, if the analytical item corresponding to the reagent-setting position is an unknown item that is not registered, a cell of the unknown item is updated to a focus state in the analytical item listing region 503 or the cell of the reagent-setting position is updated to a focus state in the detailed reagent display region 505.

Next, details of another display control in the automatic analysis device according to the embodiment of the present invention are described below using FIG. 5.

Figure 5:
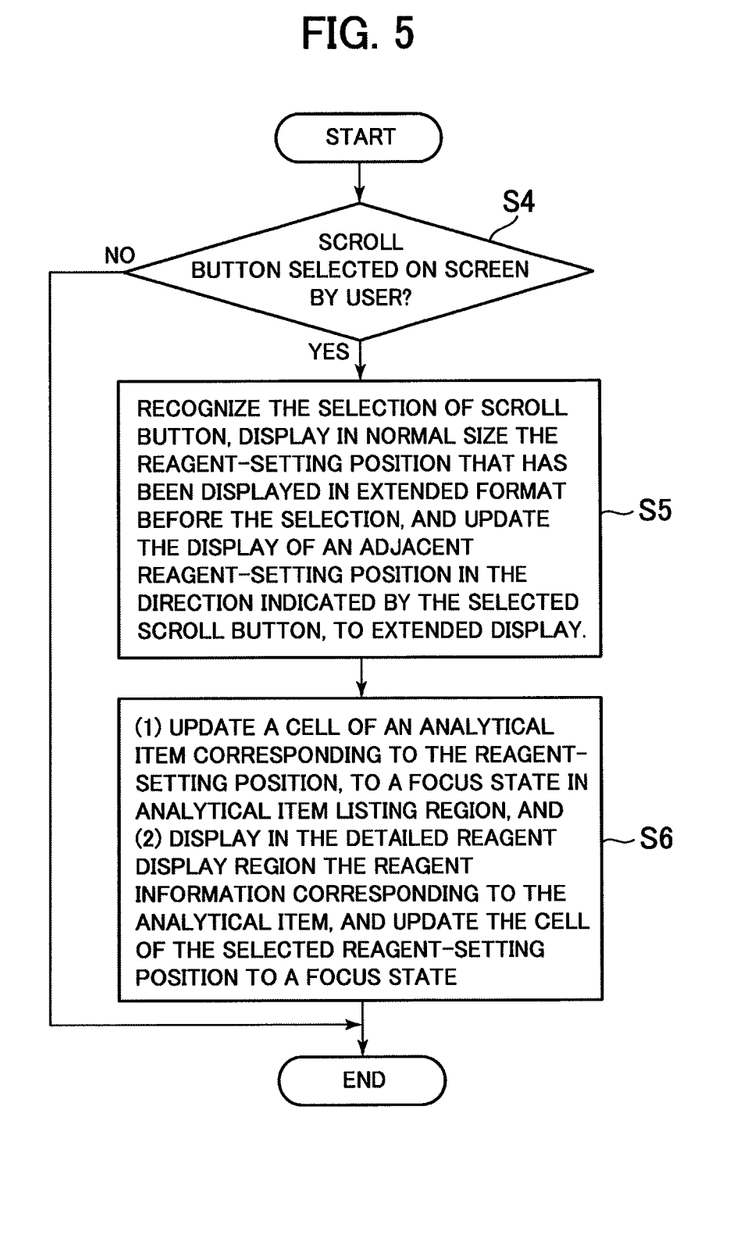
FIG. 5 is a flowchart that shows details of another display control in the automatic analysis device according to the embodiment of the present invention.

FIG. 5 is a flowchart showing the details of another display control in the automatic analysis device according to the embodiment.

FIG. 5 shows logic designed to make an enlarged display of an adjacent reagent-setting position user-selected using either scroll button on the reagent management screen, and then update corresponding cell display.

First, the user selects either scroll button on the reagent screen (step S4). Processing terminates if the selection is not conducted.

Upon recognizing the selection, the control section of the device displays in normal size the reagent-setting position that has been displayed in enlarged format before the selection, and then updates the display of a reagent-setting position adjacent to the selected scroll button, to an enlarged display format (step S5).

Next, in step S6, the control section updates the cell display of the analytical item corresponding to the reagent-setting position, to a focus state in the analytical item listing region 503. The control section further makes a detailed reagent display of the reagent information corresponding to the analytical item. At the same time, the control section updates to a focus state the cell display of the reagent information corresponding to the reagent-setting position that was selected in step S5.

As described above, in the present embodiment, the reagent-setting positions in the reagent disk are listed on the reagent management screen to enable smooth operations, and the display of a selected reagent-setting position is enlarged. Additionally, either scroll button (moving means) displayed in a size substantially equal to that of an extended display position button allows the user to easily move the mouse pointer, for example, to an anterior or posterior reagent-setting position. Even if the number of reagent positions is increased in the future, an entire set of reagent information can be confirmed on one screen without subdividing the screen and while maintaining high visibility. At the same time, any reagent-setting position can be selected efficiently.

In addition, detailed information on the selected reagent is displayed on the same screen distinctly in an operatively associated condition.

These features and characteristics enable operability to be improved without lowering visibility. In addition, even during the busiest morning hours in a laboratory, the amount of time and effort required for screen switching by click operations can be reduced very significantly, which in turn reduces a workload of the user.

Furthermore, all that is needed is just to list reagent-setting positions on a part of the reagent management screen of a conventional device and make an enlarged display of a selected reagent-setting position and scroll buttons (moving means) at its anterior and posterior positions, for which reason, screen configuration changes and software changes can be performed without a great deal of time and effort.

As described above, in the present embodiment, the reagent-setting positions in the reagent disk are listed on the reagent management screen, the display of a selected reagent-setting position is enlarged, and either scroll button (moving means) displayed in the size substantially equal to that of the extended display position button allows the user to easily move the mouse pointer, for example, to the anterior or posterior reagent-setting position. In addition to thus facilitating the selection of any reagent-setting position, therefore, the present embodiment enables the user to efficiently confirm reagent information and set up the reagent for use. This improves operability and ensures reliability of measurement results.

Moreover, in the present embodiment, all that is needed is just to list reagent-setting positions on a part of the reagent management screen of a conventional device and make an enlarged display of a selected reagent-setting position and scroll buttons (moving means) at its anterior and posterior positions, for which reason, screen configuration changes and software changes can be performed without a great deal of time and effort.

DESCRIPTION OF REFERENCE SYMBOLS

102 . . . Carriage unit
107 . . . Rack

108 ... Sample container
310 ... Reagent container
301 ... Reagent disk
309 ... Constant-temperature oven
304 ... Reaction vessel
303 ... Sample pipettor
308 ... Sample suction position
302 ... Reagent pipettor
305 ... Reaction disk
306 ... Multi-wavelength photometer
307 ... Analog/digital converter
311 ... Stirrer
312 ... Control unit
314 ... Display unit
316 ... Operating unit
312A ... Display controller
312A1 ... Extended display controller
312A2 ... Movement controller
312A3 ... Reagent status display controller
312A4 ... Synchronous display controller
501 ... Reagent position listing region
502 ... Analytical item listing region
503 ... System reagent display region
504 ... Detailed reagent display region
511 ... Reagent position buttons
512a, 512b ... Scroll buttons
513 ... Extended display position button
514 ... Reagent position numbers
515 ... Reagent status display color explanatory area

The invention claimed is:

1. An automatic analysis device comprising:
a reagent container mounting mechanism for mounting a plurality of reagent containers for containing respective reagents used for measurements at a measuring section; and
a display controller configured to display, on a display unit, a list of reagent-setting positions in the reagent container mounting mechanism, wherein the reagent-setting position list is a graphical representation including a plurality of selectable reagent-setting positions indicating a status of all reagent-setting positions in the reagent container mounting mechanism, wherein colors of individual ones of the selectable reagent-setting positions are changeable based on the status of corresponding reagent-setting positions in the reagent container mounting mechanism, wherein the display controller includes:
an extended display controller configured to display, on the display unit, in an enlarged format, a selected reagent-setting position selected from the reagent-setting position list that the display controller has displayed, the display of the selected reagent-setting position being enlarged distinctly from display of other selectable reagent-setting positions, and
a movement controller configured to enable selection of a reagent-setting position displayed next to the selected reagent-setting position being displayed in the enlarged format,
wherein the extended display controller is further configured to cause an enlarged display of, in addition to the selected reagent-setting position, an associated reagent-setting position associated with the selected reagent-setting position, wherein the associated reagent setting position includes at least one of:
a reagent-setting position including a reagent of a same kind as that of the selected reagent-setting position; or
a reagent-setting position including a reagent of a different kind from that of the selected reagent-setting position and that is used for a same analytical item.

2. The automatic analysis device according to claim 1, wherein the movement controller is configured to display, on the display unit, a scroll button at both sides of the selected reagent-setting position displayed in the enlarged format in the reagent-setting position list by the extended display controller, the movement controller further configured to display, on the display unit, the scroll buttons themselves in an enlarged format by enlarging the display of the selected reagent-setting position in the reagent-setting position list.

3. The automatic analysis device according to claim 1, wherein the display controller is configured to display, on one operating screen on the display unit, the reagent-setting position list and a list of usage status information about reagents mounted in a container-accommodated condition in the reagent container mounting mechanism.

4. The automatic analysis device according to claim 3, further comprising:
a synchronous display controller configured to cause the display unit to display, in a state operatively associated with the reagent usage status information during the display of the reagent-setting position list, usage status information about a reagent corresponding to the selected reagent-setting position selected from the reagent-setting position list.

5. The automatic analysis device according to claim 3, further comprising:
a synchronous display controller configured to cause the display unit to display, in operatively associated form in the reagent-setting position list, the selectable reagent-setting position about a reagent corresponding to the reagent of selected usage status information selected from the list of usage status information.

6. The automatic analysis device according to claim 2, wherein at least one of the scroll buttons is displayed between the selected reagent-setting position displayed in the enlarged formant and an adjacent selectable reagent-setting position displayed in a downscaled format in the reagent-setting position list.

7. An automatic analysis device comprising:
a reagent container mounting mechanism for mounting a plurality of reagent containers for containing respective reagents used for measurements at a measuring section; and
a display controller configured to display, on a display unit, a list of reagent-setting positions provided in the reagent container mounting mechanism, wherein the reagent-setting position list is a graphical representation including a plurality of selectable reagent-setting positions indicating a status of all reagent-setting positions in the reagent container mounting mechanism, wherein the display controller includes:
an extended display controller that displays, in an enlarged format, at least one selected reagent-setting position selected from the reagent-setting position list that the display controller has displayed, the display of the selected reagent-setting position being enlarged distinctly from display of other selectable reagent-setting positions,
wherein the extended display controller is further configured to cause an enlarged display of, in addition to the selected reagent-setting position, an associated reagent-setting position associated with the selected reagent-setting position, wherein the associated reagent setting position includes at least one of:
- a reagent-setting position including a reagent of a same kind as that of the selected reagent-setting position; or
- a reagent-setting position including a reagent of a different kind from that of the selected reagent-setting position and that is used for a same analytical item.

8. The automatic analysis device according to claim 7, further comprising a movement controller configured to display, on the display unit, a scroll button at both sides of the selected reagent-setting position displayed in the enlarged format in the reagent-setting position list by the extended display controller, the movement controller further configured to display, on the display unit, the scroll buttons themselves in an enlarged format by enlarging the display of the selected reagent-setting position in the reagent-setting position list.

9. The automatic analysis device according to claim 8, wherein at least one of the scroll buttons is displayed between the selected reagent-setting position displayed in the enlarged formant and an adjacent selectable reagent-setting position displayed in a downscaled format in the reagent-setting position list.

10. The automatic analysis device according to claim 7, wherein the display controller is configured to display, on one operating screen on the display unit, the reagent-setting position list and a list of usage status information about reagents mounted in a container-accommodated condition in the reagent container mounting mechanism.

* * * * *